United States Patent [19]

Chelen

[11] Patent Number: 5,234,929
[45] Date of Patent: Aug. 10, 1993

[54] METHOD OF TREATING MOTION SICKNESS WITH ANTICONVULSANTS AND ANTITUSSIVE AGENTS

[76] Inventor: William Chelen, 4396 Laclamen Dr., Centerville, Ohio 45459

[21] Appl. No.: 915,139

[22] Filed: Jul. 20, 1992

[51] Int. Cl.⁵ ............................................. A61K 31/505
[52] U.S. Cl. ..................... 514/269; 514/270; 514/271; 514/274; 514/289; 514/291; 514/386; 514/389; 514/391
[58] Field of Search ............... 514/217, 270, 271, 274, 514/386, 389, 391, 269, 289, 291

[56] References Cited

U.S. PATENT DOCUMENTS

| | | | |
|---|---|---|---|
| 2,434,635 | 1/1948 | Barrow | 514/271 |
| 4,694,010 | 9/1987 | Musacchio et al. | 514/304 |
| 4,694,010 | 9/1987 | Musacchio et al. | 514/304 |
| 4,898,860 | 2/1990 | Musacchio et al. | 514/215 |
| 4,898,860 | 2/1990 | Musacchio et al. | 514/215 |
| 4,906,638 | 3/1990 | Pontecorvo et al. | 514/282 |
| 4,906,638 | 3/1990 | Pontecorvo et al. | 514/282 |
| 4,992,443 | 2/1991 | Chelen | 514/269 |
| 4,992,443 | 2/1991 | Chelen | 514/269 |
| 5,120,739 | 6/1992 | Chelen | 514/256 |

*Primary Examiner*—S. J. Friedman
*Assistant Examiner*—William Jarvis
*Attorney, Agent, or Firm*—Larson and Taylor

[57] ABSTRACT

A method of treating or preventing motion sickness is disclosed which comprises administering an anti-motion sickness effective amount of an anticonvulsant compound such as phenytoin, ethotoin, primidone, ethosuximide or carbamazepine, in combination with a potentiating amount of an antitussive or cough suppressant agent such as dextromethorphan, levopropoxyphene, muscaphene, pholocodeine, or carbetapentene. The antitussive compounds of the present invention act as potentiating agents so as to enable effective treatment or prevention of motion sickness using a reduced amount of the anticonvulsant compound normally used in such treatment. The method of the present invention reduces the potential for various side effects and thus provides a safer and more effective method of treatment for motion sickness than prior art methods.

12 Claims, No Drawings

METHOD OF TREATING MOTION SICKNESS WITH ANTICONVULSANTS AND ANTITUSSIVE AGENTS

FIELD OF THE INVENTION

The invention relates in general to the prevention or treatment of motion sickness, and in particular to the prevention or treatment of motion sickness through the use of antitussives as potentiating agents in combination with anticonvulsant compounds.

BACKGROUND OF THE INVENTION

In the treatment of motion sickness, traditional remedies have relied predominately upon drugs in the antihistaminic and anticholinergic drug classes. See e.g. Money, *Psychological Reviews*, 50(1):1–39(1970); Wood et al., *Aerospace Med.* 43(3):249–252(1972); and Wood et al., *Aviation Environ Med.* 58(9 Supp.): A262-5(1987). Examples of these drugs include promethazine, scopolamine, dimenhydrinate, and cyclazine, and sometimes these compounds are combined with a sympathomimetic agent such as ephedrine or amphetamine to enhance their action and to reduce the side effects such as lethargy or drowsiness that often accompany the use of these drugs. Other side effects that often accompany the drugs used in the prevention of motion sickness have been blurred vision, dizziness, dryness of mouth and sedation. Thus, therapies using the present day anti-motion sickness drugs, either alone or in combination with other drugs, have been less than optimal.

More recently, it has been discovered that certain anticonvulsant agents are useful in methods to prevent or treat motion sickness. For example, in U.S. Pat. No. 4,992,443 (Chelen), a method of treating motion sickness is disclosed wherein the patient is administered an effective amount of a particular anticonvulsant compound such as diphenylhydantoin (or phenytoin), ethotoin, or primidone. Although these compounds avoid many of the problems present in the prior traditional methods for treating motion sickness, it is still a highly desirable object to reduce the amount of anticonvulsant that can effectively be administered to a patient to control motion sickness to a bare minimum so as to minimize or eliminate entirely the likelihood of side effects from the anticonvulsant compound.

Recently, researchers have revealed a brain receptor interaction between certain anticonvulsant compounds such as phenytoin and antitussives or cough supressant agents such as dextromethorphan. See Tortella et al., *Brain Research.* 383:314–318(1986). In addition, several U.S. patents including U.S. Pat. Nos. 4,694,010 and 4,898,860 (Musacchio et al.) and U.S. Pat. No. 4,906,638 (Pontecorvo et al.), disclose the use of an antitussive compound such as dextromethorphan in combination with anticonvulsant compounds in order to achieve anti-epileptic effects and control seizure. However, these references do not disclose or suggest use of the antitussive agents in the treatment of motion sickness.

It is thus a highly desirable object to develop methods of treating motion sickness through the use of reduced amounts of anticonvulsant agents which can be administered safely, conveniently and effectively in treating and/or preventing motion sickness.

It is thus another object of the present invention to prevent or treat motion sickness using an anticonvulsant compound in combination with a potentiating agent which allows successful use of a reduced amount of the anticonvulsant compound in the treatment of motion sickness with a resulting reduced risk of side effects as well.

SUMMARY OF THE INVENTION

These and other objects of the present invention are obtained by administering to a patient susceptible to or suffering from motion sickness an anti-motion sickness effective amount of at least one compound having the structure:

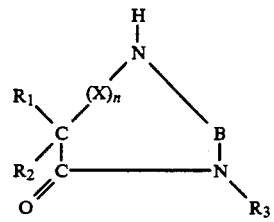

wherein $R_1$, $R_2$ and $R_3$ are H, aliphatic or aromatic groups, B is —C=O or —CH$_2$—, n' is 0 or 1, and X is

or its non-toxic, pharmaceutically acceptable acid addition salts; along with a potentiating amount of an antitussive compound such as dextromethorphan.

In the anticonvulsant compound of the invention, $R_1$, $R_2$ and $R_3$ can be similar or dissimilar, and often comprise a mixture of hydrogen, an aromatic group and an aliphatic group. Suitable aromatic groups for the $R_1$, $R_2$ and $R_3$ groups include aryl groups of six to twelve carbon atoms, preferably phenyl, and suitable aliphatic groups include alkyl groups of one to five carbon atoms. Particularly preferred as the anticonvulsant compounds of the present invention are phenytoin, ethotoin and primidone. Other anticonvulsants suitable for use in the present invention include compounds such as ethosuximide and carbamazepine. In the preferred embodiment, the antitussive compounds are administered in an amount that potentiates the anti-motion sickness effect of the anticonvulsant, and preferably are selected from opioid derivatives such as dextromethorphan (the dextro-isomer of the codeine analog of the narcotic levorphanol), levopropoxyphene, noscapine, and pholocodine, and from non-opioid agents such as carbetapentane (see, e.g., Goodman, *The Pharmacological Basis of Therapeutics*, 1990).

The term "motion sickness" as used in the specification and appended claims includes airsickness, seasickness, space motion sickness, ground vehicle sickness (e.g. car sickness, etc.), flight simulator sickness, and earth sickness (the symptoms of motion illness when returning to earth or solid ground after flying in space, water-born travel, etc., also known as "mal de demarquement"). The present invention is an improvement over past treatments of motion sickness, particularly in that agents in the anticonvulsant class capable of stabilizing neuronal membranes and/or reducing polysynaptic responses so as to alleviate the effects of motion sickness can now be combined with an antitussive potentiating agent which allows for effective motion-sickness treatment using reduced amounts of the anticonvulsant agents. The reduction in the effective amount anticonsulvant that is required through the method of the invention reduces the tendency for possible side effects, and thus allows for safer treatment of motion sickness than that provided by prior art methods.

DETAILED DESCRIPTION OF THE PREFERRED EMBODIMENT

In accordance with the present invention, an effective composition for treating and/or preventing motion sickness is provided by combining an anticonvulsant compound with an antitussive agent in an amount effective to potentiate the anti-motion sickness activity of the anticonvulsant compound and allow effective treatment of motion sickness using approximately one-half the usual anti-seizure dose of the anticonvulsant. It is particularly preferred that the antitussive used in the present invention comprises dextromethorphan, the dextro-isomer of the codeine analog of the drug levorphanal, but other antitussive agents such as levopropoxyphene, nosoapine, pholocodine, and carbetapentane can also be used in the invention. The antitussive agents should be employed in an amount which is effective in potentiating the anti-motion sickness effect of the anticonvulsant agent, and in general this amount will comprise about one to three milligrams per kilogram of body weight of the antitussive agent as individually required. It will be clear to one skilled in the art that the preferred amount of the antitussive agent used will depend on the compound selected and the individual needs of the patient.

In the preferred embodiment, the anticonvulsant agent used in an anti-motion sickness effective amount comprises a compound having the structure

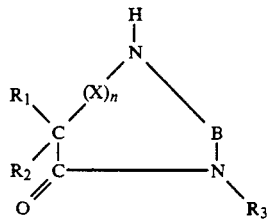

wherein $R_1$, $R_2$ and $R_3$ are H, aliphatic or aromatic groups, B is —C═O or —CH$_2$—, n' is 0 or 1, and X is

or its non-toxic, pharmaceutically acceptable acid add salts. Examples of suitable acids for the non-toxic, pharmaceutically acceptable acid addition salts include inorganic acids such as hydrochloric acid, hydrobromic acid, nitric acid, sulfuric acid, and phosphoric acid; organic acids such as formic acid, acidic acid, propreonic acid, benzoic acid, maleic acid, fumaric acid, succinic acid, daturic acid, citric acid, oxalic acid, glyoxylic acid, and aspartic acid; alkane sulfonic acids such as methansulfonic acid and ethansulfonic acid; arylsulfonic acids such as benzynesulfonic acid and p-toluenesulfonic acid; and the arylcarboxylic acids.

The anticonvulsant compounds used to treat anti-motion sickness in accordance with the present invention are at least those described in U.S. Pat. No. 4,992,443 (Chelen), incorporated herein by reference, and include such compounds as phenytoin, ethotoin, primidone, ethosuximide, and carbamazepine. Ideally, patients susceptible to or suffering from motion sickness are administered an anti-motion sickness effective amount of the anticonvulsant at a strength approximately one-half of the common anti-seizure dose that would be needed if the potentiating agent of the present invention was not employed. In the present invention, doses of the anticonvulsant of approximately three to ten milligrams per kilogram of body weight of an anticonvulsant agent such as phenytoin is all that is necessary to achieve effective anti-motion sickness effects when used with the potentiating amount of the antitussive compound of the invention. Although the actual dosage needed will vary among individual patients, the effective dosage of the anticonvulsant when used in combination with an antitussive agent in accordance with the present invention will be less than half the normal anticonvulsant dose that would be needed without the potentiating factor.

It is also contemplated that the compositions of the invention can be used in any suitable pharmaceutical carrier known in the art. Suitable excipients for pharmaceutical carriers that can be used in accordance with the invention include talc, arabic gum, lactose, starch, magnesium stearate, cocoa butter, aqueous and non-aqueous vehicles, fatty bodies of animal or vegetable origin, paraffinic derivatives, glycols, diverse wetting agents, dispersants or emulsifiers and preservatives.

The active compounds of the present invention can be administered to any patient susceptible to motion sickness which can be any warm-blooded animal including man, either before or after the onset of motion sickness symptoms. The administration can be effected orally, intramuscularly, intravenously, or in any other suitable manner that would be known to a skilled practitioner in the art. The usual daily dosage will depend on the subject treated and the particular compound administered along with the particular method of administration. In general, an administered dosage of three to ten milligrams per kilograms of body weight of the anticonvulsant agent such as phenytoin along with the administration from one to three milligrams per kilogram of body weight of an antitussive such as dextromethorphan will generally be suitable to achieve anti-motion sickness effects in a patient with greatly reduced chance for the side effects that might accompany higher dosage of the anticonvulsants.

The following example is presented as illustrative only of the present invention and is not to be construed as limiting the invention in any respect:

EXAMPLE

Motion sickness susceptible subjects were treated with either a placebo or an anticonvulsant/antitussive combination consisting of phenytoin and dextromethorphan. A dosage of seven milligrams per kilogram of phenytoin (less than half the anticonvulsant dose) was administered in two divided doses (approximately 300 milligrams and 200 milligrams) over several hours. One to two hours later, a dose of two milligrams per kilogram of dextromethorphan (150 to 175 milligrams) was administered to the patients. Subjects were then exposed to Coriolis stimulation through a full range of active head motions in a rotating chair in an identical manner for trials including patients receiving the placebo as well as those receiving the anticonvulsant/antitussive combination.

In the untreated trial runs wherein patients had received the placebo, severe nausea was induced within an average of twelve minutes of the Coriolis stimulation. However, for patients having undergone the anticonvulsant/antitussive therapy, subjects endured a period of Coriolis stimulation a mean duration greater than five times as long as in the trials with patients receiving the placebos. In some of these latter trials, the Coriolis stimulation was discontinued because after a prolonged period only minimal motion sickness symptoms could be induced in those patients receiving the anticonvulsant/antitussive compounds of the present invention. The anticonvulsant/antitussive combinations of the invention thus proved effective in the treatment of motion sickness using reduced amounts of the anticonvulsant compound than that employed in previous treatments.

What is claimed is:

1. A method of treating or preventing motion sickness comprising administering to a patient susceptible to or suffering from motion sickness an anti-motion sickness effective amount of a compound having the structure:

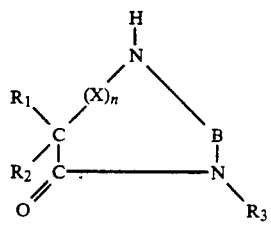

wherein $R_1$, $R_2$ and $R_3$ are H, aliphatic or aromatic groups; B is —C=O or —CH$_2$—; n' is 0 or 1; and X is

or its non-toxic pharmaceutically acceptable acid addition salts;
in combination with an antitussive compound in an amount effective to potentiate the anti-motion sickness activity of the anticonvulsant compound.

2. A method according to claim 1 wherein $R_1$ and $R_2$ are aromatic groups.

3. A method according to claim 2 wherein the aromatic groups are phenyl groups.

4. A method according to claim 1 wherein $R_1$ is an aromatic group and $R_2$ is H.

5. A method according to claim 4 wherein $R_1$ is phenyl.

6. A method according to claim 1 wherein $R_3$ is aliphatic.

7. A method according to claim 6 wherein $R_3$ is alkyl.

8. A method according to claim 1 wherein the anticonvulsant compound is selected from the group consisting of diphenylhydantoin, ethotoin, primidone, ethosuximide, and carbamazepine.

9. A method according to claim 1 wherein the antitussive compound comprises an opioid derivative selected from the group consisting of dextromethorphan, levopropoxyphene, noscapine and pholocodine.

10. A method according to claim 1 wherein the antitussive compound comprises carbetapentane.

11. A method according to claim 1 wherein the anti-motion sickness effective amount of the anticonvulsant compound comprises about three to ten milligrams per kilogram of body weight of the patient treated.

12. A method according to claim 1 wherein the amount of the antitussive compound effective to potentiate the anti-motion sickness effect of the anticonvulsant agent comprises about one to three milligrams per kilogram of body weight of the patient.

* * * * *